United States Patent [19]

Fertel et al.

[11] Patent Number: 4,954,639

[45] Date of Patent: Sep. 4, 1990

[54] SINGLE POT PROCESS FOR MAKING A FLUOROANTHRANILIC ACID

[75] Inventors: Lawrence B. Fertel, Kenmore; Neil J. O'Reilly, Grand Island, both of N.Y.

[73] Assignee: Occidental Chemical Corporation, Niagara Falls, N.Y.

[21] Appl. No.: 399,131

[22] Filed: Aug. 28, 1989

[51] Int. Cl.[5] .............................................. C07D 209/48
[52] U.S. Cl. ..................... 548/475; 562/456; 562/458
[58] Field of Search ................. 562/458, 456; 548/475

[56] References Cited

U.S. PATENT DOCUMENTS

| | | | |
|---|---|---|---|
| 3,832,364 | 8/1974 | Coulson | 562/458 |
| 3,847,974 | 11/1974 | Sturm et al. | 562/458 |
| 4,232,459 | 11/1980 | Kilpper et al. | 562/458 |
| 4,374,266 | 2/1983 | Fifolt et al. | 562/458 |
| 4,521,616 | 6/1985 | Fifolt | 562/453 |

OTHER PUBLICATIONS

An article by Villiger, V. in *Chem. Ber.*, vol. 1909, pp. 3529-3549.

*Primary Examiner*—James H. Reamer
*Attorney, Agent, or Firm*—James F. Tao; Richard D. Fuerle

[57] ABSTRACT

Disclosed is a method of making ionized fluoroanthranilic acid from a fluorophthalic compound in a single pot process without isolating any intermediate product. A composition is prepared which comprises an aqueous solution of water, a fluorophthalic compound selected from the group consisting of

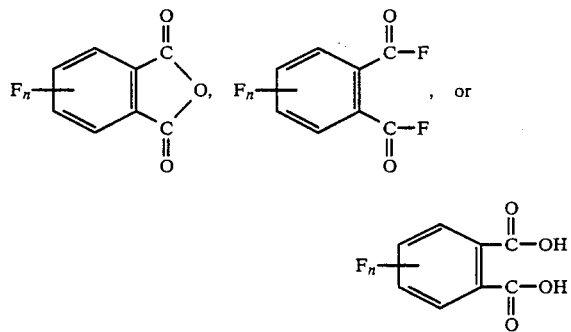

and mixtures thereof, where "n" is 1 to 4, at a concentration of about 5 to about 30 percent by weight based on the water weight, and about 1 to about 1.5 equivalents of hydroxylamine or a mineral acid salt thereof. The pH of the composition is maintained at at least about 11 and the temperature of the composition is maintained at at least about 90° C. The unionized form of the acid is made by cooling below 50° C. and lowering the pH to between about 4 and about 5. Also disclosed are the intermediate compounds, fluoro-N-hydroxyphthalimides, and a method of making them.

20 Claims, No Drawings

SINGLE POT PROCESS FOR MAKING A FLUOROANTHRANILIC ACID

BACKGROUND OF THE INVENTION

This invention relates a method of making a fluoroanthranilic acid. In particular, it relates to a method of making 4,5-difluoroanthranilic acid from 4,5-difluorophthalic anhydride in a single pot process without isolating any intermediate product.

The compound 4,5-difluoroanthranilic acid (DFAA) can be used as a pharmaceutical intermediate for making antibacterials. Previously, DFAA was made by treating 4,5-difluorophthalic anhydride (DFPAN) with ammonia to produce 4,5-difluorophthalamic acid (DFPA), which underwent a Hofmann rearrangement when treated with an aqueous solution of sodium hypochlorite in the presence of a base to lead ultimately, after acidification, to DFAA:

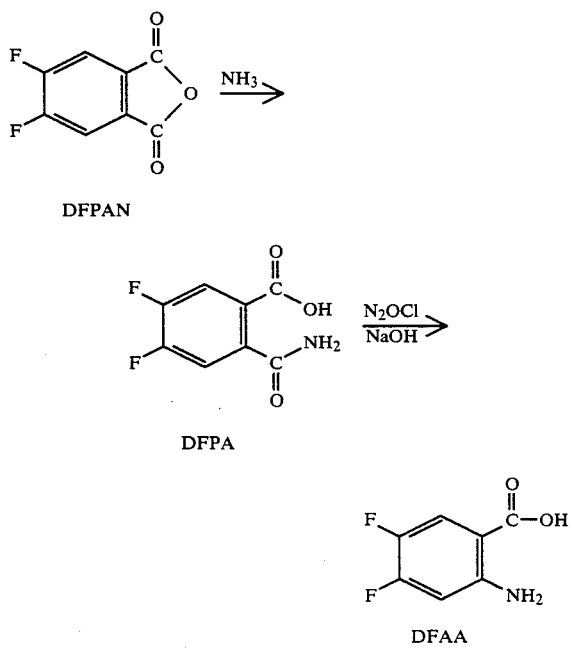

That reaction is described in U.S. Pat. No. 4,521,616.

Although that reaction works well on a laboratory scale, it presents several difficulties on scaling up. Specifically, the maximum amount of bleach (i.e., active NaOCl) that can be used in the reaction cannot exceed 15% because more concentrated bleach solutions are not stable. Therefore, relatively high dilution conditions are needed for the reaction to run successfully. In addition, because of the high dilutions that are needed, the cost of the aqueous disposal system is excessive.

SUMMARY OF THE INVENTION

We have discovered that DFAA can be made from DFPAN in a single pot process without isolating any intermediate product. This is accomplished by maintaining the pH of the reaction at at least about 11 and the temperature of the reaction at at least about 90° C. The use of a single pot simplifies the process of this invention and reduces its costs, as does not isolating intermediates. Compared to the prior process of making DFAA, the process of this invention has a higher throughput because more concentrated solutions can be used. In addition, a minimal amount of waste is produced by the process of this invention, and the waste that is produced is easy to dispose of.

While the process of this invention does not require the isolation of an intermediate, an intermediate, a fluoro-N-hydroxyphthalimide, is nevertheless produced which is novel and which can be isolated if desired. These novel intermediates can be used in peptide synthesis.

DESCRIPTION OF THE INVENTION

In the process of this invention an aqueous solution is prepared of a fluorophthalic compound, water, and hydroxylamine or a mineral acid salt thereof. The fluorophthalic compounds used in the process of this invention have the general formulas

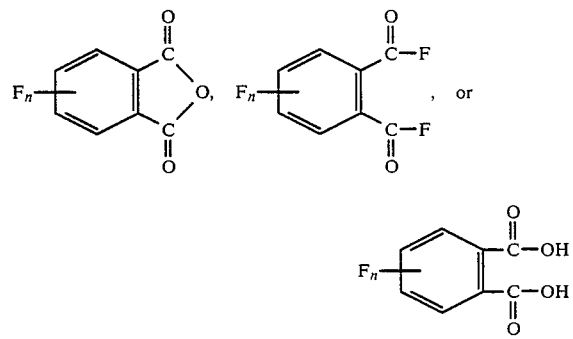

where "n" is 1 to 4.

In the preferred compounds, "n" is 2, and most preferably the two ring fluorines are in the 4,5 position, as the product, DFAA, is most useful in making antibacterials. The preferred starting material is DFPAN because it is less expensive and is easier to work with. Fluorines are required rather than other halogens in order to make the ultimate antibacterial products. The amount of fluorophthalic compound in the solution should be about 5 to about 30 percent by weight, based on the weight of the water, and should preferably be about 20 to about 25 percent by weight. Higher percentages may present insolubility problems and lower percentages are an inefficient utilization of the reactor vessel.

The reaction requires the presence of hydroxylamine ($NH_2OH$), or a mineral acid salt thereof. While an aqueous solution of hydroxylamine can be used, it is preferable to use a mineral acid salt of hydroxylamine because the acid salts are easier and safer to handle. Mineral acids that can be used to form mineral acid salts of hydroxylamine include, for example, hydrochloric acid, sulfuric acid, hydrobromic acid, and phosphoric acid. The preferred acid salts are the hydrochloride salt and the sulfate salt, as those salts are readily available, easy to handle, and readily soluble in water. The hydroxylamine or mineral acid salt thereof should be used at a concentration of about 1 to about 1.5 equivalents based on the fluorophthalic compound.

The reaction that occurs in the process of this invention, using DFPAN as the starting material and producing the intermediate 4,5-difluoro-N-hydroxyphthalimide (DFHP), is as follows:

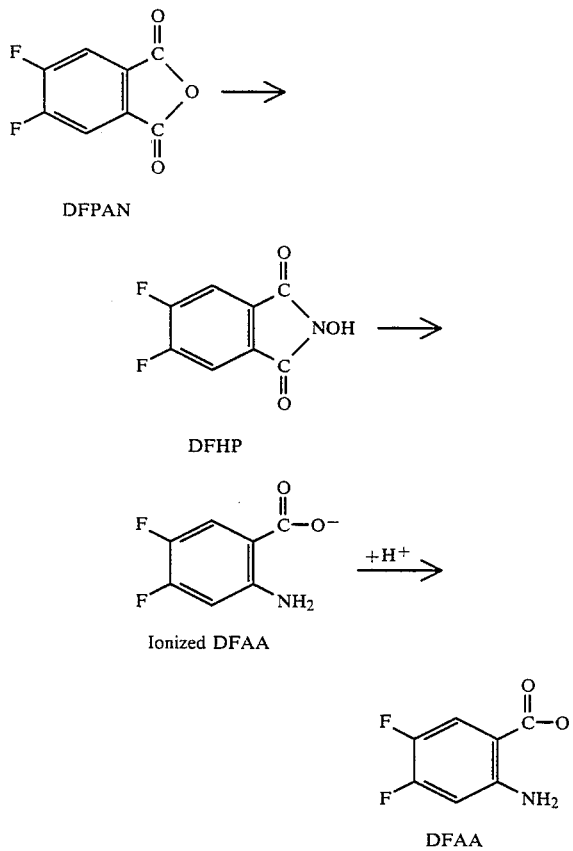

DFPAN

DFHP

Ionized DFAA

DFAA

The fluoro-N-hydroxyphthalimide intermediate compound will correspond to the starting material in the number and position of ring fluorides, and any of the fluorophthalic compounds can be used to make a fluoro-N-hydroxyphthalimide intermediate.

In conducting the reaction it is important to begin with and maintain the pH of the reaction mixture at greater than 11 and the temperature at greater than 90° C. If the pH is permitted to fall much below about 11, the intermediate product may be formed. If the intermediate forms, it can produce a foam which can exceed the capacity of the reactor vessel, disrupting the process. Maintaining the pH at greater than 11 can be accomplished by monitoring the pH and making periodic additions of a water soluble base. (If it is desired to intentionally form and collect the intermediate, this can be accomplished by using only about 1 equivalent of the base per equivalent of hydroxylamine or mineral acid salt thereof, e.g., 1 mole of base per mole of hydroxylamine hydrochloride or 2 moles of base per mole of hydroxylamine sulfate.) Examples of suitable bases include inorganic compounds such as sodium hydroxide, potassium hydroxide, sodium carbonate, potassium carbonate, sodium bicarbonate, etc. Sodium hydroxide or potassium hydroxide is preferred because they are particularly effective in preventing the formation of the intermediate, thereby preventing the formation of foam. The temperature of the reaction mixture should be maintained at at least 90° C. because, while the reaction will occur at lower temperatures, it proceeds too slowly. Since the reaction mixture is an aqueous solution, the maximum temperature of the reaction mixture is about 100° C. The reaction can be monitored by taking aliquots, acidifying the aliquots to a pH below 1, and following the progress of the reaction by loss of starting material on a gas chromatogram.

When the ionized form of the fluoroanthranilic acid has been formed, the unionized form can be made by cooling the solution to below about 50° C. and preferably to room temperature, and then adding a mineral acid (preferably the same mineral acid used to form the salt of hydroxylamine). Sufficient mineral acid should be added to lower the pH to between about 4 and about 5. If the pH is greater than 5 the product acid may not be fully protonated, and if the pH is lowered to below about 4, the amine salt of product acid may be produced. The solid product acid is insoluble in cool water and precipitates. It can be filtered and washed with water or re-precipitated from hot water to purify it, and it can be used in the production of antibacterials or other products such as dyestuff and pesticides.

The following examples further illustrate this invention:

EXAMPLE 1

Preparation of 4,5-difluoro-N-hydroxyphthalimide (a) Using sodium carbonate:

4,5-difluorophthalic anhydride (2.0 g, 0.0109 mol) was combined with sodium carbonate (0.71 g, 0.0068 mol) in 5 mL of water. Hydroxylamine hydrochloride (0.9 g, 0.0129 mol) was added portionwise to the stirred mixture at 0° C, and a white precipitate of the hydroxamic acid formed. The reaction mixture was then heated to 60°–70° C. After 1 hour the initial precipitate dissolved, and after 0.25 hour, a new precipitate appeared. The reaction was cooled to 0° C., filtered and washed with a small amount of cold water. After drying in a dessicator, 1.09 g of product was collected. Gas chromatogram-mass spectrometer (GCMS) analysis indicated 86% product, 8% starting material, and 6% 4,5-difluorophthalimide. The molecular weights were consistent with the product analysis.

(b) Using sodium hydroxide:

Sodium hydroxide (0.24 g, 0.006 mol) was combined with hydroxylamine hydrochloride (0.5 g, 0.006 mol) in 5 mL of water and heated to 60° C. DFPAN (1.0 g, 0.0055 mol) was added and the solution was heated to 90°–100° C. After 1 hour, a precipitate formed, and was analyzed as being 75% of the desired 4,5-difluoro-N-hydroxyphthalimide.

EXAMPLE 2

Conversion of 4.5-difluoro-N-hydroxyphthalimide to DFAA

The difluoro-N-hydroxyphthalimide of Example 1 (2.1 g, 0.01 mol), was combined with sodium carbonate (0.65 g, 0.0062 mol) in 10 mL water. The solution was heated to reflux for 1 hour. After cooling to room temperature, the mixture was acidified to pH 4–5 with hydrochloric acid. Filtration, washing with water, and drying led to 1.26 g of 4,5-difluoroanthranilic acid (mp. 174°–178° C.). The structure was completely consistent with nuclear magnetic resonance (NMR) and mass spectral analysis.

EXAMPLE 3

Preparation of 4,5-difluoroanthranilic acid (a) Two steps, one pot:

Sodium hydroxide (0.24 g, 0.006 mol) was combined with hydroxylamine hydrochloride (0.5 g, 0.006 mol) in 5 mL of water and heated to 60° C. DFPAN (1.0 g, 0.0055 mol) was added and the solution was heated to 90°-100° C. After 1 hour, a precipitate formed. At this point, an additional 0.5 g NaOH was added to the reaction mixture, and heated to reflux. Cooling and acidification with concentrated hydrochloric acid followed by filtration led to 0.48 g (51%) of DFAA.

(b) One step reactions:

Sodium hydroxide (7.5 g, 0.19 mol) and hydroxylamine hydrochloride (5.4 g, 0.0781 mol) were combined in 100 mL of water. 4,5-difluorophthalic anhydride (11.5 g, 0.062 mol) was added, and the reaction was heated to 90°-100° C. for 0.5 hour. The reaction was cooled, and acidified with HCl to a pH between 4 and 5. The precipitate was collected and dried to yield 10.2 g (91%) of 4,5-difluoroanthranilic acid.

Sodium hydroxide (65 g, 1.63 mol) and hydroxylamine hydrochloride (47.2 g, 0.679 mol) were combined in 500 mL of water. 4,5-difluorophthalic anhydride (100 g., 0.543 mol) was added, and the reaction was heated to 90°-100° C. for 0.5 hour. The reaction was cooled, and acidified with HCl to pH 7. Glacial acetic acid, which has a pH between 4 and 5, was added (70 mL) to fully precipitate the product. Isolation as usual led to 51.09 g (54%) of DFAA.

Sodium hydroxide (6.5 g, 0.163 mol) and hydroxylamine sulfate (4.9 g, 0.029 mol) were combined in 40 mL of water. 4,5-difluorophthalic anhydride (10 g, 0.0543 mol) was added, and the reaction was heated to reflux for 0.5 hour. The reaction was cooled and acidified to a pH between 4 and 5 with a 50% sulfuric acid solution. Isolation led to 6.67 g (71%) of 4,5-difluoroanthranilic acid.

We claim

1. A method of making an ionized fluoroanthranilic acid comprising
    (A) preparing an aqueous solution of
       (1) a fluorophthalic compound selected from the group consisting of

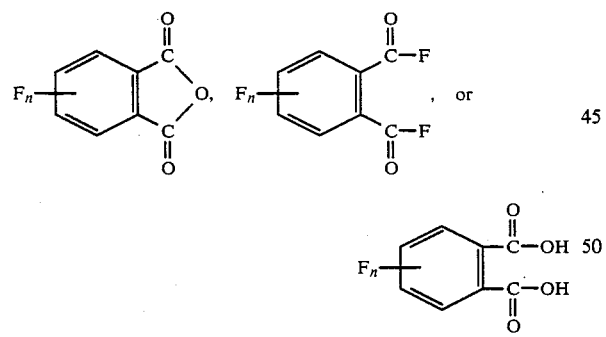

and mixtures thereof, where "n" is 1 to 4, at a concentration of about 5 to about 30% by weight, based on the weight of water in said solution; and
       (2) about 1 to about 1.5 equivalents of a hydroxylamine compound selected from the group consisting of hydroxylamine and mineral acid salts thereof; and
    (B) maintaining the pH of said solution at at least about 11 and the temperature of said solution at at least 90° C. where said method is performed in a single pot without isolating any intermediate product.

2. A method according to claim 1 wherein "n" is 2.

3. A method according to claim 2 wherein said fluorophthalic compound is selected from the group consisting of

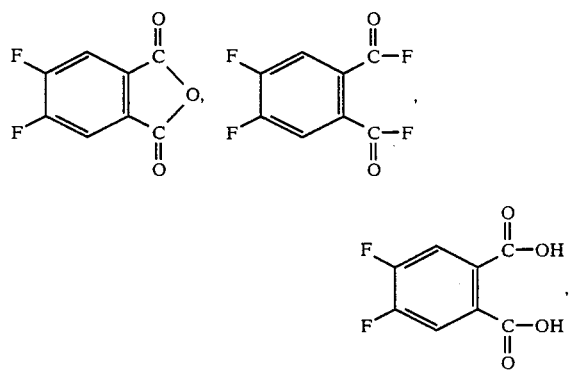

and mixtures thereof.

4. A method according to claim 3 wherein aid fluorophthalic compound has the formula

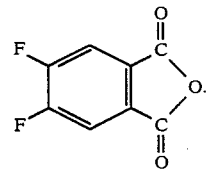

5. A method according to claim 1 wherein the concentration of said fluorophthalic compound is about 20 to about 25% by weight, based on the weight of said water.

6. A method according to claim 1 wherein said hydroxylamine compound is a mineral acid salt of hydroxylamine.

7. A method according to claim 6 wherein said mineral acid salt of hydroxylamine is hydroxylamine hydrochloride or hydroxylamine sulfate.

8. A method according to claim 1 wherein said pH is maintained by the addition of an inorganic base.

9. A method according to claim 8 wherein said inorganic base is an alkali metal hydroxide.

10. A method according to claim 9 wherein said alkali metal hydroxide is sodium hydroxide or potassium hydroxide.

11. A method according to claim 1 including the additional last steps of cooling said solution and lowering its pH to about 4 to about 5.

12. A method according to claim 11 wherein said solution is cooled below 50° C.

13. A method according to claim 11 wherein said pH is lowered with a mineral acid.

14. A method of making 4,5-difluoroanthranilic acid from 4,5-difluorophthalic anhydride comprising
    (A) preparing an aqueous solution of
       (1) 4,5-difluorophthalic anhydride at a concentration of about 5 to about 30% by weight, based on the weight of water in said solution; and
       (2) about 1 to about 1.5 equivalents of a compound selected from the group consisting of hydroxylamine and mineral acid salts thereof; and
    (B) maintaining the pH of said solution at at least about 11 and the temperature of said solution at at least 90° C., where said method is performed in a single pot without isolating any intermediate product.

15. A method of making a fluoro-N-hydroxyphthalimide comprising
(A) preparing an aqueous solution of
(2) a fluorophthalic compound selected from the group consisting of

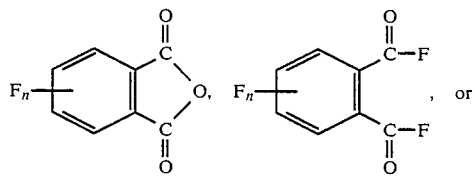

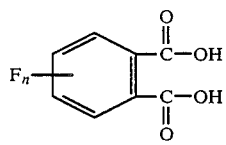

and mixtures thereof, wherein "n" is 1 to 4, at a concentration of about 5 to about 30% by weight, based on the weight of water in said solution;
(2) about 1 to about 1.5 equivalents of a hydroxylamine compound selected from the group consisting of hydroxylamine and mineral acid salts thereof; and
(3) about 1 equivalent of a water soluble base, based on said hydroxylamine compound; and
(B) maintaining the pH of said solution at less than about 11 and the temperature of said solution at at least 90° C.

16. A method according to claim 15 wherein "n∞ is 2.

17. A method according to claim 16 wherein said compound is selected from the group consisting of

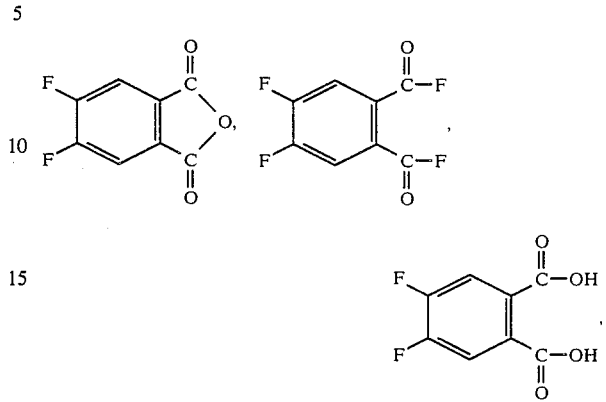

and mixtures thereof.

18. A method according to claim 17 wherein said compound has the formula

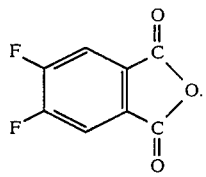

19. A method according to claim 15 including the additional last step of raising the pH to at least about 11.

20. A method according to claim 15 wherein said hydroxylamine compound is hydroxylamine hydrochloride or hydroxylamine sulfate.

* * * * *